United States Patent [19]

Hentschel et al.

[11] 4,271,299

[45] Jun. 2, 1981

[54] PROCESS FOR THE PRODUCTION OF 2-ALKOXY-4,6-DICHLORO-S-TRIAZINES

[75] Inventors: Klaus Hentschel, Kalmthout, Belgium; Friedrich Bittner, Bad Soden, Fed. Rep. of Germany

[73] Assignee: Deutsche Gold- und Silber-Scheideanstalt vormals Roessler, Frankfurt, Fed. Rep. of Germany

[21] Appl. No.: 94,479

[22] Filed: Nov. 15, 1979

[30] Foreign Application Priority Data

Nov. 20, 1978 [DE] Fed. Rep. of Germany ....... 2850339

[51] Int. Cl.$^3$ .......................................... C07D 251/26
[52] U.S. Cl. .................................... 544/218
[58] Field of Search ......................................... 544/218

[56] References Cited

U.S. PATENT DOCUMENTS

| | | | |
|---|---|---|---|
| 2,911,337 | 11/1959 | Uhlenbroek et al. | 544/218 |
| 3,198,797 | 8/1965 | Dexter et al. | 544/218 |
| 3,925,377 | 12/1975 | Geiger et al. | 260/248 |

FOREIGN PATENT DOCUMENTS 1670731 12/1970 Fed. Rep. of Germany.
2332636 1/1975 Fed. Rep. of Germany.

OTHER PUBLICATIONS

Ullmann, Enzyklpadie der technishen Chemie, 3rd Ed. (1954), vol. 1, pp. 743–744; 769–770.

*Primary Examiner*—John M. Ford
*Attorney, Agent, or Firm*—Cushman, Darby & Cushman

[57] ABSTRACT

2-Alkoxy-4,6-dichloro-s-triazines are produced by the known reaction of cyanuric chloride with an alcohol in the presence of an acid binding agent in an improved manner by working at high mixing velocities and thus at high reaction speed and thereby obtaining high throughputs in small tubular containers by introducing liquid cyanuric chloride through a nozzle in the upper portion of the mixing apparatus in countercurrent flow to upwardly flowing reactants (plus acid binding agent) introduced from at least one lower nozzle above a breast shaped constriction in the lower, open portion of the apparatus. The process can be carried out at normal, reduced or elevated pressure.

7 Claims, 3 Drawing Figures a
PROCESS FOR THE PRODUCTION OF 2-ALKOXY-4,6-DICHLORO-S-TRIAZINES

BACKGROUND OF THE INVENTION

It is known to react cyanuric chloride with an alcohol or phenol in such manner than one halogen atom is replaced by an ether group.

In this connection it is important that the cyanuric chloride is reacted with the alcohol in the presence of an acid binding agent as e.g. sodium hydroxide, potassium hydroxide, sodium bicarbonate, potassium bicarbonate, alkali phosphate, e.g. sodium phosphate, sodium hydrogen phosphate, sodium hydrogen phosphate, potassium phosphate or an organic base, e.g. collidine. The reaction can also be carried out with sodium alcoholate solution, e.g. in benzene.

In all reactions of this type attention should be paid on the one hand that the reaction does not fall into the acid range or on the other hand, that the reaction become to alkaline. In both cases hydrolysis of the cyanuric chloride is to be expected. In the strong acid range the alkoxy triazine can react to form cyanuric acid and alkali chloride. This reaction, depending on the temperature, can even go explosively.

It has been become desirable to have a process according to which substituted 2-alkoxy-4,6-dichloro-s-triazines are producible continuously in high purity.

SUMMARY OF THE INVENTION

Figure 1:
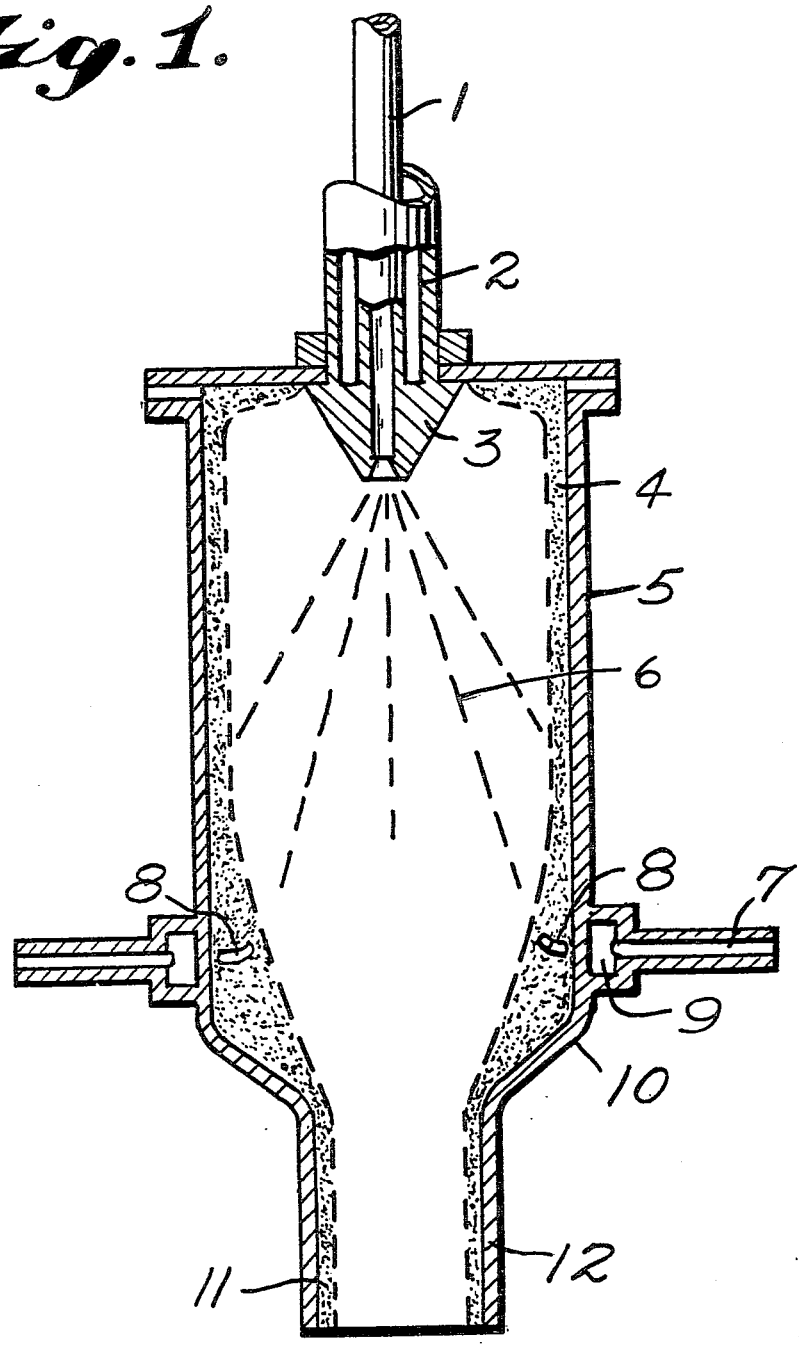
FIG. 1 is a vertical sectional elevation of one form of apparatus suitable for carrying out the process of the invention.

It has now been found that substituted 2-alkoxy-4,6-di-chloro-s-triazines can be produced continuously by reaction of cyanuric chloride and an alcohol or alcoholates in the presence of an acid binding agent if liquid cyanuric chloride which is preferably free from chlorine and cyanogen chloride is sprayed into a container at temperatures in its molten range, if necessary in the presence of an inert gas, through a nozzle, preferably a spray nozzle, which is located in the head of a tubular container, during which this tubular container is closed or closeable at the top and downward constricted breast shaped to a discharge opening and with which the other reactant or reactants discharges through one or preferably several nozzles, preferably polished steel nozzles, which are located above the constriction and consist of one or more tangential spray agencies arranged in one or more rows which are arranged slightly above in the direction of the upper closing device or are arranged in the direction of the nozzle located in the upper portion and form a liquid layer along the entire chamber walls up to the nozzle for the cyanuric chloride, whereby the thickness of this layer at the breast shaped restriction is greater than at the rest of the chamber walls, and in which the sprayed cyanuric chloride enters.

The liquid cyanuric chloride is preferably introduced into the nozzle through a heated conduit.

By using the described apparatus it is possible to so distribute the alcohol or alcoholate, the acid acceptor and solvent at the chamber walls that the liquid layer at the shaped constriction is thicker than at the remaining chamber walls.

By the expression used in the glass art: "breast shaped constriction" is meant a constriction which does not proceed steeply, but in a first S curve going from the wall of the tubular container to the discharge opening. Corresponding constrictions are also present in red wine bottles at the transition from the true bottle to the neck.

The constriction in the tubular container can preferably always begin where about 50% of the sprayed particles meet the liquid layer built up on the wall. Preferably this is the case in the lower third of the tubular container.

The size of the diameter of the discharge opening of itself is not critical. Naturally it depends on the viscosity of the medium being discharged and must have at least such a size that air can enter.

The discharge opening is preferably converted into a discharge tube which has any desired diameter, preferably however, the same diameter or larger than the discharge opening.

The nozzle or nozzles for the alcohol or alcoholate, solvent and acid acceptor to be sure can be arranged at any place in the tubular container above the constriction, but preferably are located in the region directly above the breast shaped constriction.

As the tangentially arranged spray agencies, there can be used small tubes or nozzles as well as openings in the chamber walls or, with the presence of a feed ring, in its chamber walls.

Preferably there are used small tubes.

The tubular container described has the great advantage that it can be operated not only at an atmospheric pressure but also at reduced pressure. Thus without doing anything further it permits the adjustment proceeding from atmospheric pressure to reduced pressure of 0.01 bar.

At reduced pressure a portion of the solvent evaporates through which a cooling of the solution or suspension forming takes place. The mixing and reaction temperature in this way lets itself be held readily to a low level which is very essential for a continuous procedure.

As alcohols and alcoholates which can be reacted with cyanuric chloride there can be employed compounds of the formula R—OH or R—OM where R is an alkyl, cycloalkyl, alkenyl, alkinyl or aralkyl group with 1–18 carbon atoms or such a group substituted by halogen, e.g. chlorine or bromine, lower alkoxy, e.g. of 1–4 carbon atoms, lower alkoxy, e.g. of 1–4 carbon atoms, lower alkoxy lower alkoxy e.g. with 1–4 carbon atoms in each alkoxy group, lower alkylthio, e.g. with 1–4 carbon atoms in the alkyl group or aryloxy and M is an alkali metal, e.g. sodium or potassium. Thus there can be used methanol, ethanol, propanol, isobutanol, pentanol, isopentanol, 2-methyl-butan-1-ol, n-hexanol, 2,2-dimethyl pentanol-1, 2-chloroethanol (ethylene chlorohydrin) 3-chloropropanol-1, 2-methoxyethanol, 2-ethoxyethanol, 2-propoxyethanol, 2-n-butoxyethanol, 2-methoxypropanol-1, 3-methoxypropanol-1, 3-ethoxypropanol-1, 3-methoxybutanol-1, 2-(2-methoxyethoxy)-ethanol, 2-(2-ethoxyethoxy)ethanol, 2-ethylmercaptoethanol, 2-phenoxyethanol, cyclohexylmethanol, 2-buten-1-ol, allyl alcohol, propargyl alcohol, isoporpanol, sec. butyl alcohol, hexanol-2, 1-methoxypropanol-2, 1,3-diethoxypropanol-2, 3-methylbutanol-2, pentanol-3, cyclopentanol, cyclohexanol, 2-methylcyclohexanol, n-butanol, benzyl alcohol, anisyl alcohol, octanol, octadecanol, decanol, dodecanol, methallyl alcohol, crotyl alcohol, oleyl alcohol, 2-bromoethanol, butoxyethanol, butoxybutanol, butoxyethoxyethanol, sodium methylate, potassium methylate, sodium ethylate, potassium ethylate, sodium butylate, sodium octadecanoxide, sodium allylate, sodium benzylate.

As acid binding agents, there can likewise be used those known in the art, e.g., alkali hydroxides such as NaOH or KOH or alkali carbonates and bicarbonates such as sodium carbonate, potassium carbonate, sodium bicarbonate, potassium bicarbonate.

Since the cyanuric chloride is present in liquid form, it is not necessary to employ a solvent for it, however, it is favorable that the alcohol and above all the alcoholate be supplied to the nozzles. As solvents there can be used organic solvents which are indifferent, i.e. do not take part in the reaction and which are preferably miscible with water. The reaction takes place suitably at room temperature or moderately elevated temperature, i.e. preferably between 10° and 50° C. wherein the stoichiometric ratio must be so selected that there is substantially prevented the formation of the dialkoxy-s-triazine.

A suitable apparatus for the recovery of the mentioned chloro-amino-s-triazines is described and claimed in Hentschel application Ser. No. 94,803, filed Nov. 15, 1979 and entitled "Apparatus For Bringing Liquids In Contact" which is operated in the following manner.

As shown in FIG. 1, the liquid cyanuric chloride in supply line 1 is led through a coaxial heater 2 via a unary or binary nozzle 3 into the mixing chamber 5, i.e., the tubular container 5.

Figure 2:
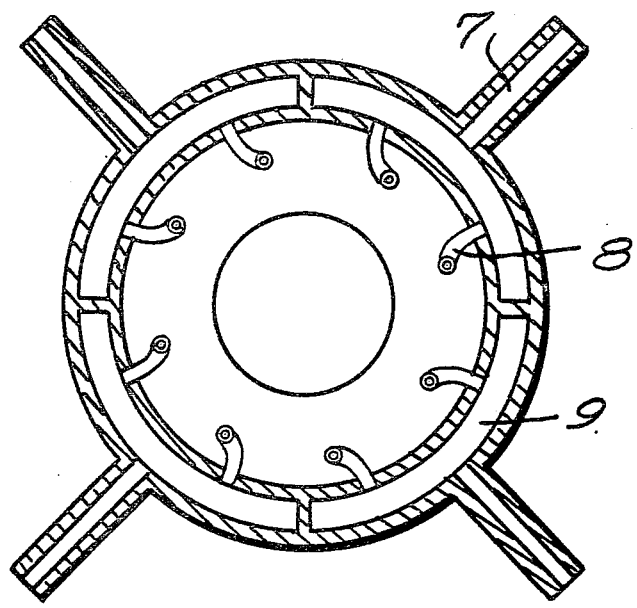
FIG. 2 is a cross-sectional view along the line 2—2 of FIG. 1.

The components are being brought into contact with the sprayed cyanuric chloride through separate lines 7 into a distribution ring having separate chamber segments 9, see also FIG. 2. The components are injected tangentially from these chamber segments via the slightly upwardly directed spray systems into the mixing chamber 5.

When using only one supply and only one spray opening into the mixing chamber 5, the supply 7 passes directly into the spray opening 8 and the segmented chamber 9 is eliminated.

Besides the component in the circumferential direction, the solvent jet has a velocity component in the axial direction. Therethrough the liquid reaches the wall of the mixing chamber 5. There it builds a liquid layer 4.

If liquids are supplied through the supply lines 7, 8 and 9 into the mixing chamber 5, there occurs here an intensive thorough mixing of the supplied liquids, whose intensity can be increased still more by introducing a gas or vapors of the solvent via the spray system 8.

The cyanuric chloride leaving the nozzle 3 is sprayed into the liquid layer 4. The spray angle for the cyanuric chloride sprayed out of nozzle 3 can be between 15° and 150°, preferably between 15° and 120°.

The shape of the spray varies from hollow or solid cone up to an unarranged mist, according to the type of nozzle.

With the entering of the spray particles 6 the sprayed cyanuric chloride reacts in the liquid layer. The energy brought in is given up to the liquid layer, independent of the pressure in the tubular container.

The discharging mixture which leaves the tubular container 5 through the discharge opening 12 goes to the container 14 which can be connected if desired detachably, either directly or indirectly via line 13 to the discharge opening 12 of the container 5.

Figure 3:
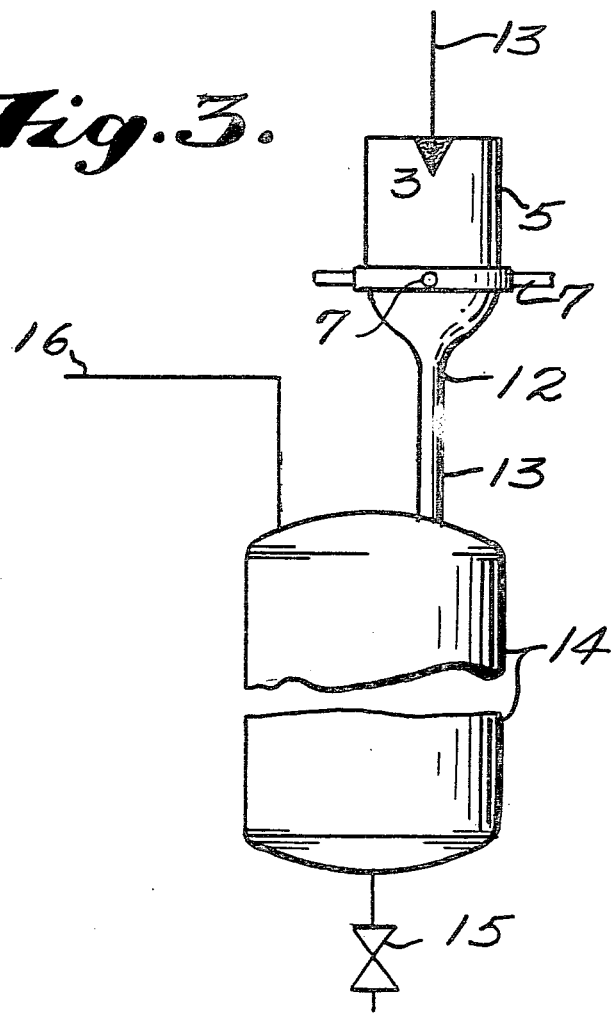
FIG. 3 is a schematic view of apparatus for carrying out the invention.

In this way it is possible to establish any desired pressure, i.e., any reduced or excess pressure, in the tubular container 5 and container 14 through known apparatus which is connected with the container 14 via line 16, see FIG. 3. (However, the known apparatuses for regulating the pressure are not shown in FIG. 3.)

The mixture is withdrawn at the discharge valve 15. The container 14, however, can in a given case also serve as reaction container for a further treatment or reaction.

However, it is also possible to apply reduced or superatmospheric pressure directly into the discharge line 13 through the known apparatuses and to transport away in known manner the discharging mixture from line 13 while eliminating an intermediate connection from container 14.

The apparatuses 5 and 14 shown in FIGS. 1 and 3, in a given case also line 13, can be heated or cooled in known manner, according to the requirements, see, e.g., Ullmann, Enzyklopadie der technischen Chemie, Vol. 1, 3rd Edition, 1951, pages 743–744 and 769–770.

Likewise there can be used for this purpose the known construction materials, loc. cit.

The volume of the tubular container 5 is determined by the properties of the liquid used whereby the path of the sprayed particles 6 up to the impingement on the liquid layer 4 should be held as short as possible.

Through this it is possible to carry out relatively small throughputs in a very small tubular container, e.g., the volume in Example 1 is about 0.5 liters. By establishing a specific pressure, e.g., a reduced pressure in mixing chamber 5, the heat energy and heat of reaction of the sprayed cyanuric chloride in contact with the liquid layer can be removed.

The product produced leaves the mixing chamber through the discharge outlet 12.

To improve the formation of the liquid layer the spray systems 8 tangential to the mixing chamber are directed slightly upwardly. The exact angle of bending is so adjusted according to the solvent that the liquid layer reaches up to the nozzle, but does not touch it.

Through the breast shaped constriction and the thicker liquid layer produced at this wall position thereby there results, despite the outlet opening, that the remaining chamber walls always are covered with a uniform, i.e., uninterrupted layer of liquid. Through this there is guaranteed a high mixing velocity.

The spray cone of the liquid cyanuric chloride is designated by the number 6.

The number of inlet lines 7 depends on the particular case.

Thus in feeding in the components one supply line is sufficient, however, for better distribution of these components there has also proven as desirable to use several supply lines, see for example FIG. 2; even using several liquids which also can be simultaneously introduced as a mixture the distribution ring described for example in FIG. 2 is suitable, in a given case there can be connected a further reaction space.

If the residence time in the mixing chamber is not sufficient for the complete reaction of the reactants then there can be provided a subsequent reaction section.

Liquid cyanuric chloride can be obtained according to known process, e.g., according to Geiger, German Pat. No. 2,322,636 and related Geiger U.S. Pat. No.

3,925,377. The entire disclosure of the Geiger U.S. patent is hereby incorporated by reference and relied upon.

Preferably according to the process of the invention there is employed a liquid cyanuric chloride whose temperature is 170° C. and which is free from chlorine and cyanogen chloride. For freeing from chlorine and cyanogen chloride known processes are suitable, as, e.g., dephlegmatization.

Unless otherwise indicated all parts and percentages are by weight.

The process can comprise, consist essentially of or consist of the steps set forth and the material can comprise, consist essentially of or consist of those set forth.

The invention will be further explained through the following example.

DESCRIPTION OF THE PREFERRED EMBODIMENT

EXAMPLE 1

Liquid cyanuric chloride at about 170° C. was led via the heated supply line 1 into the unary nozzle 3. The nozzle had a bore of 0.8 mm and a spray angle of about 70°. The supply pressure of the melt was 4 bar. There were sprayed through the nozzle 45 kg/h of cyanuric chloride into the mixing chamber 5. The mixing chamber 5 had a diameter of 80 mm and atmospheric pressure prevailed in it.

Methylene chloride in an amount of 585 liters/h via two opposed supply lines 7 via four small tubes 8 reached the mixing chamber 5 and through a different supply line 7, 30 kg/h of 2,4,6-trimethyl pyridine reached the mixing chamber 5 and through four supply lines 7 there were introduced into the mixing chamber 9.9 l/h of methanol.

After a residence time of 1 hour the solution was removed, washed with water and the 2-methoxy-4,6-dichloro-s-triazine isolated from the organic phase. The yield amounted to 99%.

What is claimed is:

1. A process for the production of 2-alkoxy-4, 6-dichloro-s-triazine by reacting cyanuric chloride with an alcohol or alcoholate in the presence of an acid binding agent comprising spraying cyanuric chloride downwardly and outwardly at a temperature in its molten range from the upper portion of a vertical tubular zone closed at the top thereof to contact and mix with the other reactant or reactants which form a liquid layer defining said tubular zone, constricting said layer in a breast-shaped manner downwardly below the place of entry of the cyanuric chloride into the tubular zone to form a narrower discharge opening, discharging said other reactant or reactants as a spray tangentially to said layer and directed slightly upwardly in the direction of the closed top above said constriction and below the point of introduction of the cyanuric chloride and thereby forming said liquid layer along the entire tubular zone to the point of introduction of the cyanuric chloride, whereby the thickness of said layer where it is formed in the breast-shaped constriction is greater than it is in the remainder of the tubular zone.

2. The process of claim 1 wherein the liquid cyanuric chloride employed is free from chlorine or cyanogen chloride.

3. A process according to claim 9 wherein the alcohol or alcoholate has the formula R—OH or R—OM where R is an alkyl, cycloalkyl, alkenyl, alkinyl or aralkyl group with 1–18 carbon atoms or such a group substituted by halogen, lower alkoxy, lower alkoxy lower alkoxy, lower alkylthio, or aryloxy and M is an alkali metal.

4. A process according to claim 3 wherein R is alkyl, cycloalkyl, alkenyl or aralkyl.

5. A process according to claim 4 wherein in the reactant employed R is methyl.

6. The process of claim 1 including reducing the pressure to between below atmospheric pressure and 0.01 bar and thereby lowering the mixing and reaction temperature.

7. A process according to claim 1 comprising discharging the reaction mixture formed to another container adapted for use at subatmospheric or superatmospheric pressure.

* * * * *